United States Patent — Stone

(10) Patent No.: US 12,090,300 B2
(45) Date of Patent: Sep. 17, 2024

(54) SYSTEM AND METHOD FOR CONTROLLING OXYGEN DELIVERY TO IMPLANTED CELLS

(71) Applicant: Giner Life Sciences, Inc., Newton, MA (US)

(72) Inventor: Simon G. Stone, Arlington, MA (US)

(73) Assignee: GINER, INC., Newton, MA (US)

(*) Notice: Subject to any disclaimer, the term of this patent is extended or adjusted under 35 U.S.C. 154(b) by 1114 days.

(21) Appl. No.: 16/412,281

(22) Filed: May 14, 2019

(65) Prior Publication Data

US 2019/0343616 A1 Nov. 14, 2019

Related U.S. Application Data

(60) Provisional application No. 62/671,298, filed on May 14, 2018.

(51) Int. Cl.
A61F 2/02 (2006.01)
A61K 48/00 (2006.01)
(Continued)

(52) U.S. Cl.
CPC ......... A61M 5/14276 (2013.01); A61F 2/022 (2013.01); A61K 48/0075 (2013.01);
(Continued)

(58) Field of Classification Search
CPC .... A61M 5/14276; A61M 2005/14204; A61M 2202/0208; A61M 2205/04;
(Continued)

(56) References Cited

U.S. PATENT DOCUMENTS 5,814,151 A 9/1998 Lee et al.
5,944,661 A 8/1999 Swette et al.
(Continued)

FOREIGN PATENT DOCUMENTS

CN 101123984 A 2/2008
CN 105792775 A 7/2016
(Continued)

OTHER PUBLICATIONS

International Search Report mailed Sep. 17, 2019, from corresponding PCT Application No. PCT/US19/32296.
(Continued)

Primary Examiner — Robert J Utama
Assistant Examiner — Hamza A Darb
(74) Attorney, Agent, or Firm — KRIEGSMAN & KRIEGSMAN

(57) ABSTRACT

Method and system for controlling oxygen delivery to a cell implant. In one embodiment, the system includes a water electrolyzer, a cell capsule, a gas conduit, a total fluid pressure sensor, and a controller. The water electrolyzer generates gaseous oxygen with a variable output. The cell capsule includes a cell chamber adapted to hold cells. The gas conduit interconnects the water electrolyzer and the cell capsule to deliver gaseous oxygen generated by the water electrolyzer to the cell capsule. The total fluid pressure sensor is positioned at a location that provides a representative reading of the total fluid pressure within the cell chamber. The controller is electrically coupled both to the total fluid pressure sensor and to the water electrolyzer so that the controller may control the variable output of the water electrolyzer based on one or more sensed total pressure readings from the total fluid pressure sensor.

20 Claims, 9 Drawing Sheets

(51) Int. Cl.
*A61M 5/142* (2006.01)
*A61M 39/02* (2006.01)
*C25B 1/04* (2021.01)

(52) U.S. Cl.
CPC ...... *C25B 1/04* (2013.01); *A61M 2005/14204* (2013.01); *A61M 39/0208* (2013.01); *A61M 2202/0208* (2013.01)

(58) Field of Classification Search
CPC .... A61M 2205/3344; A61M 2005/006; A61M 5/142; A61M 5/16804; A61M 5/16877; A61M 5/172; A61M 5/486; A61M 2202/0078; A61M 2202/02; A61M 2205/0216; A61M 2205/0227; A61M 2205/33; A61M 2205/3327; A61M 2205/331; A61F 5/022; A61K 48/0075; C25B 1/04; Y02E 60/36; C12N 5/0018; C12N 2500/02

See application file for complete search history.

(56) References Cited

U.S. PATENT DOCUMENTS

| | | |
|---|---|---|
| 6,179,986 B1 | 1/2001 | Swette et al. |
| 6,368,592 B1 | 4/2002 | Colton et al. |
| 6,811,905 B1 | 11/2004 | Cropley et al. |
| 7,811,433 B2 | 10/2010 | Manoukian et al. |
| 7,892,222 B2 | 2/2011 | Vardi et al. |
| 8,083,821 B2 | 12/2011 | Tempelman et al. |
| 8,282,811 B2 | 10/2012 | Kosek et al. |
| 8,444,630 B2 | 5/2013 | Rotem et al. |
| 8,551,670 B2 | 10/2013 | Mittelsteadt et al. |
| 8,784,389 B2 | 7/2014 | Stern et al. |
| 9,357,764 B2 | 6/2016 | Tempelman et al. |
| 9,595,727 B2 | 3/2017 | Mittelsteadt et al. |
| 10,091,985 B2 | 10/2018 | Tempelman et al. |
| 10,231,817 B2 | 3/2019 | Tempelman et al. |
| 10,557,691 B2 | 2/2020 | Stone et al. |
| 11,033,666 B2 | 6/2021 | Ferrante et al. |
| 2003/0087427 A1 | 5/2003 | Colton et al. |
| 2005/0136092 A1 | 6/2005 | Rotem et al. |
| 2009/0149874 A1 | 6/2009 | Ortiz et al. |
| 2010/0196439 A1 | 8/2010 | Beck et al. |
| 2010/0330547 A1 | 12/2010 | Tempelman et al. |
| 2011/0054387 A1 | 3/2011 | Stern et al. |
| 2012/0178150 A1* | 7/2012 | Tempelman ......... A01N 1/0226 435/307.1 |
| 2015/0112247 A1* | 4/2015 | Tempelman ............ A61F 2/022 435/283.1 |
| 2016/0022180 A1* | 1/2016 | Joseph ............... A61B 5/14532 600/366 |
| 2018/0125399 A1 | 5/2018 | Joseph et al. |
| 2018/0133383 A1 | 5/2018 | Ferrante et al. |
| 2018/0135948 A1* | 5/2018 | Stone ................ A61K 48/0075 |
| 2018/0318566 A1 | 11/2018 | Ferrante et al. |
| 2019/0328289 A1 | 10/2019 | Papas |
| 2019/0336267 A1 | 11/2019 | Tempelman et al. |
| 2019/0368056 A1 | 12/2019 | Schwenk et al. |
| 2022/0054318 A1 | 2/2022 | Schwenk et al. |
| 2022/0152369 A1 | 5/2022 | Schwenk et al. |

FOREIGN PATENT DOCUMENTS

| | | |
|---|---|---|
| EP | 1645243 A2 | 4/2006 |
| JP | 2017200612 A | 11/2017 |
| WO | 200050851 A1 | 8/2000 |
| WO | 0150983 A1 | 7/2001 |
| WO | 2006122169 A2 | 11/2006 |
| WO | 2008079997 A2 | 7/2008 |
| WO | 2009031154 A2 | 3/2009 |
| WO | 2015048184 A1 | 4/2015 |
| WO | 2018085714 A1 | 5/2018 |
| WO | 2018102077 A1 | 6/2018 |
| WO | 2018144098 A1 | 8/2018 |
| WO | 2018144099 A1 | 8/2018 |

OTHER PUBLICATIONS

Written Opinion mailed Sep. 17, 2019, from corresponding PCT Application No. PCT/US19/32296.

Akesson et al., "Control of Dissolved Oxygen in Stirred Bioreactors," Technical Reports TFRT-7571, Department of Automatic Control, Lund Institute of Technology, Lund, Sweden (1998).

Sandmaier et al., "A Square-diaphragm piezoresistive pressure sensor with a rectangular central boss for low-pressure ranges," IEEE transactions on electron devices, 40(10):1754-1759 (1993).

Yu et al., "Chronically Implanted Pressure Sensors: Challenges and State of the Field," Sensors: 14:20620-20644 (2014).

Sander et al., "A Monolithic Capacitive Pressure Sensor with Pulse-Period Output," IEEE Transactions on Electron Devices, 27(5):927-930 (1980).

Zeman et al., "Evaluation of Oxygen Permeability of Polyethylene Films," Technical Sciences, 15(2):331-345 (2012).

GlySens glucose monitor, GlySens Incorporated, San Diego, California, https://glysens.com/, accessed Oct. 20, 2022.

* cited by examiner

SYSTEM AND METHOD FOR CONTROLLING OXYGEN DELIVERY TO IMPLANTED CELLS

CROSS-REFERENCE TO RELATED APPLICATIONS

The present application claims the benefit under 35 U.S.C. 119(e) of U.S. Provisional Patent Application No. 62/671,298 inventor Simon G. Stone, filed May 14, 2018, the disclosure of which is incorporated herein by reference.

BACKGROUND OF THE INVENTION

The present invention relates generally to implantable medical devices useful in cell and/or tissue therapy applications and relates more particularly to systems and methods for controlling oxygen delivery to cells that are implanted in a subject using implantable medical devices.

Implantable medical devices (or "implant devices") are commonly-employed tools used in the treatment of various diseases, disorders, and/or conditions. Some implant devices comprise therapeutic cells and/or tissues that are encapsulated within an implantable container or capsule. The implantable container or capsule is typically designed to allow cells and/or tissues to produce a desired therapeutic and to disseminate the produced therapeutic to the patient while, at the same time, limiting an immunological response.

An example that illustrates the need for cell or tissue implantation is the development of cellular therapies for the treatment of diabetes. Currently, cell-based treatment options for diabetes treatment include whole pancreas organ transplant or transplant of pancreatic islets of Langerhans. However, because of the need for lifelong immunosuppressive treatment, these therapies are typically reserved for patients with the most difficult to treat Type 1 diabetes, particularly those who are already receiving immunosuppressive therapy as a result of a previous or concurrent organ transplant.

To address this shortcoming, containers or capsules have been developed that enable the implantation of islets and other tissues without the need for immunosuppression. For example, some currently available cell capsules incorporate an immunoisolating membrane that protects allogenic encapsulated tissue from the host immune system. Unfortunately, however, such an immunoisolating membrane also prevents vascularization of the encapsulated tissue, thereby making the delivery of essential gases to the encapsulated tissue and the removal of waste gases therefrom more difficult. As a result, such approaches have ultimately failed to realize the anticipated benefits due, in part, to limitations in oxygen delivery to the encapsulated cells.

In an attempt to address the above-noted limitations in oxygen delivery to implanted cells, several methods for delivering oxygen to cell capsules are being developed. These methods include the periodic injection of compressed gaseous oxygen through the skin to an implanted device, the delivery of oxygen to cell capsules through a percutaneous catheter, the implantation of chemical oxygen generators, and the implantation of electrochemical oxygen generating devices.

An example of an approach that involves the periodic injection of compressed gaseous oxygen through the skin to an implanted device containing cells is disclosed in U.S. Pat. No. 8,784,389 B2, inventors Stern et al., which issued Jul. 22, 2014, and which is incorporated herein by reference. More specifically, according to the aforementioned patent, there is disclosed a method for replenishing gas in a subcutaneously implanted medical device containing functional cells, the method comprising: inserting at least one needle, adapted to penetrate the skin and connecting a subcutaneously implanted medical device; connecting the inserted at least one needle to a gas replenishing apparatus; extracting gas from a gas reservoir in the implanted device into the gas replenishing apparatus; sensing oxygen level in the extracted gas; calculating the amount of gas needed for replenishing oxygen in the reservoir based on the sensed oxygen level in the extracted gas; and supplying gas from a gas tank in the gas replenishing apparatus to the gas reservoir in the implanted device.

The present inventor believes that the above approach has certain limitations. For example, the injection of pressurized oxygen requires that the user pierce the skin on a periodic basis and also requires periodic replacement of the septum in the device. Also, the failure to properly penetrate the septum with the needle could introduce gaseous oxygen to unwanted areas of the body, which may be hazardous. Additionally, the percutaneous delivery of oxygen carries a risk of infection, and associated devices are undesirably exposed to the environment. Moreover, importantly, the oxygen level in the gas reservoir is not sensed on a continuous or automatic basis, but rather, is only sensed when the needle is inserted by an operator into the gas reservoir. According to the above-discussed patent, the insertion of the needle into the gas reservoir may be as infrequent as once every two weeks. As can be appreciated, with such infrequent monitoring of the oxygen levels, it is possible that dangerously low or high levels of oxygen may not be sensed, and addressed, in a timely fashion.

An example of an approach that involves the use of an implanted electrochemical oxygen generator to provide oxygen to an implant device containing cells is disclosed in U.S. Pat. No. 10,231,817 B2, inventors Tempelman et al., which issued Mar. 19, 2019, and which is incorporated by reference. More specifically, according to the aforementioned patent, there is disclosed a system for gas treatment of a cell implant, the system including, in one embodiment, (i) an electrochemical device configured to output a first gas, such as gaseous oxygen (ii) a cell containment subsystem comprising a first chamber configured to receive cells, and (iii) a gas conduit for conveying the first gas from the electrochemical device to the first chamber, the gas conduit being coupled at one end to the electrochemical device and at an opposite end to the first chamber. According to another embodiment, the cell containment subsystem includes both a gas chamber and cell chambers on one or both sides of the gas chamber. In the aforementioned embodiment, the gas chamber receives the first gas from the electrochemical device, and the first gas is then delivered from the gas chamber to the one or more cell chambers.

The amount of oxygen that is provided in a system of the type described above should ideally be exactly equal to what is needed to sustain the respiratory needs of all of the implanted cells and to allow for increased cell density in the cell containment subsystem. However, in practice, matching the amount of oxygen that is needed with the amount of oxygen that is provided is difficult to accomplish. In those cases where too little oxygen is provided, the implanted cells may die or fail to perform their full functions. On the other hand, because a fully implanted device typically has no percutaneous vent for unused gas, in those cases where too much oxygen is provided, the gas pressure experienced by the cell containment subsystem may be excessive. In fact, in some instances, the gas pressure may become sufficiently great as to cause the cell containment subsystem to swell and to be at a significant risk for rupture.

Another example of an approach that involves the use of an implanted electrochemical oxygen generator to provide oxygen to an implant device containing cells is disclosed in PCT International Publication No. WO 2018/085714 A1, which was published May 11, 2018, and which is incorporated by reference. More specifically, according to the aforementioned publication, there is disclosed an encapsulation device system for therapeutic applications, such as, but not limited to, regulating blood glucose. The system may comprise an encapsulation device with a first oxygen sensor integrated inside the device and a second oxygen sensor disposed on an outer surface of the device, wherein the sensors allow for real-time measurements (such as oxygen levels) related to cells (e.g., islet cells, stem cell derived beta cells, etc.) housed in the encapsulation device. The system may also feature an exogenous oxygen delivery system operatively connected to the encapsulation device via a channel, wherein the exogenous oxygen delivery system is adapted to deliver oxygen to the encapsulation device.

As can be appreciated, the approach described in the aforementioned PCT publication requires the use of oxygen sensors. However, oxygen sensors are typically sophisticated devices that rely on complicated techniques like fluorescence decay or voltammetric sensing (i.e., Clark electrode) to selectively detect a particular chemical species, in this case, oxygen. Moreover, an oxygen sensor may not give sufficient feedback to the control system regarding excessive gas pressure or sudden leaks.

Other documents that may be of interest include the following, all of which are incorporated herein by reference: U.S. Pat. No. 8,444,630 B2, inventors Rotem et al., issued May 21, 2013; U.S. Pat. No. 7,892,222 B2, inventors Vardi et al., issued Feb. 22, 2011; U.S. Pat. No. 6,368,592 B1, inventors Colton et al., issued Apr. 9, 2002; U.S. Patent Application Publication No. US 2018/0318566 A1, inventors Ferrante et al., published Nov. 8, 2018; U.S. Patent Application Publication No. US 2018/0135948 A1, inventors Stone et al., published May 17, 2018; U.S. Patent Application Publication No. US 2018/0133383 A1, inventors Ferrante et al., published May 17, 2018; U.S. Patent Application Publication No. 2010/0330547 A1, inventors Tempelman et al., published Dec. 30, 2010; US 2005/0136092 A1, inventors Rotem et al., published Jun. 23, 2005; U.S. Patent Application Publication No. US 2003/0087427 A1, inventors Colton et al., published May 8, 2003; PCT International Publication No. WO 2018/144099 A1, published Aug. 9, 2018; PCT International Publication No. WO 2018/144098 A1, published Aug. 9, 2018; PCT International Publication No. WO 2018/102077 A2, published Jun. 7, 2018; PCT International Publication No. WO 2009/031154 A2, published Mar. 12, 2009; PCT International Publication No. WO 2008/079997 A2, published Jul. 3, 2008; PCT International Publication No. WO 2006/122169 A2, published Nov. 16, 2006; PCT International Publication No. WO 01/50983 A1, published Jul. 19, 2001; and Akesson, M., & Hagander, P., "Control of Dissolved Oxygen in Stirred Bioreactors," Technical Reports TFRT-7571, Department of Automatic Control, Lund Institute of Technology (LTH) (1998).

SUMMARY OF THE INVENTION

It is an object of the present invention to provide a novel system for controlling oxygen delivery to implanted cells.

According to one aspect of the invention, there is provided a system for controlling oxygen delivery to a cell implant, the system comprising (a) a water electrolyzer, the water electrolyzer being configured to generate gaseous oxygen with a variable output; (b) a first cell capsule, the first cell capsule comprising a cell chamber adapted to hold cells; (c) a first gas conduit, the first gas conduit fluidically coupled to the water electrolyzer and to the first cell capsule, whereby gaseous oxygen generated by the water electrolyzer is delivered to the first cell capsule; (d) a first total fluid pressure sensor, the first total fluid pressure sensor being placed so as to sense the total fluid pressure within the cell chamber of the first cell capsule; and (e) a controller, the controller being electrically coupled both to the first total fluid pressure sensor and to the water electrolyzer, wherein the controller is configured to control the variable output of the water electrolyzer based on one or more sensed total pressure readings from the first total fluid pressure sensor.

In a more detailed feature of the invention, the first total fluid pressure sensor may be disposed within the first cell capsule.

In a more detailed feature of the invention, the first cell capsule may comprise a gas compartment and a cell compartment, and the gas compartment and the cell compartment may be in gas communication with one another.

In a more detailed feature of the invention, the first total fluid pressure sensor may be disposed within the gas compartment of the first cell capsule.

In a more detailed feature of the invention, the first total fluid pressure sensor may be disposed outside of the first cell capsule.

In a more detailed feature of the invention, the first gas conduit may be tee-shaped, with a first end of the gas conduit fluidically coupled to the water electrolyzer, with a second end of the gas conduit fluidically coupled to the first total fluid pressure sensor, and with a third end of the gas conduit fluidically coupled to the first cell capsule.

In a more detailed feature of the invention, the system may further comprise a second gas conduit, and the second gas conduit may have a first end fluidically coupled to the water electrolyzer and a second end fluidically coupled to the first total fluid pressure sensor.

In a more detailed feature of the invention, the system may further comprise a second gas conduit, and the second gas conduit may have a first end fluidically coupled to the first cell capsule and a second end fluidically coupled to the first total fluid pressure sensor.

In a more detailed feature of the invention, the system may further comprise a second cell capsule, the second cell capsule may have a cell chamber adapted to hold cells, and the first gas conduit may be further fluidically coupled to the second cell capsule, whereby gaseous oxygen generated by the water electrolyzer may be delivered to the second cell capsule.

In a more detailed feature of the invention, the system may further comprise a second total fluid pressure sensor, the second total fluid pressure sensor may be electrically coupled to the controller, the gas conduit may be a manifold comprising a first end fluidically coupled to the water electrolyzer, a second end fluidically coupled to the first cell capsule, a first branch fluidically coupled to the first total fluid pressure sensor, and a second branch fluidically coupled to the second total fluid pressure sensor, and the gas conduit may be constricted between the first and second branches and may have an opening sized so that a difference in pressures sensed by the first and second total fluid pressure sensors is indicative of fluid flow therepast.

According to another aspect of the invention, there is provided a system for controlling oxygen delivery to a cell implant, the system comprising (a) a water electrolyzer, the water electrolyzer being configured to generate gaseous oxygen with a variable output; (b) a first cell capsule, the first cell capsule comprising a cell chamber adapted to hold cells; (c) a first total fluid pressure sensor; (d) a first gas conduit, the first gas conduit fluidically coupled to the water electrolyzer and to the first total fluid pressure sensor; (e) a second gas conduit, the second gas conduit fluidically coupled to the first total fluid pressure sensor and to the first cell capsule, whereby gaseous oxygen generated by the water electrolyzer is delivered to the first cell capsule via the first gas conduit, the first total fluid pressure sensor, and the second gas conduit; and (f) a controller, the controller being electrically coupled both to the first total fluid pressure sensor and to the water electrolyzer, wherein the controller is configured to control the variable output of the water electrolyzer based on one or more sensed total pressure readings from the first total fluid pressure sensor.

It is also an object of the present invention to provide a novel method for controlling oxygen delivery to implanted cells.

According to one aspect of the invention, there is provided a method for controlling delivery of a gas to a cell implant, the method comprising the steps of (a) providing an electrolyzer, the electrolyzer having a variable gas output; (b) providing a cell capsule, the cell capsule comprising a cell chamber adapted to hold cells, wherein the cell capsule is fluidically coupled to the variable gas output of the electrolyzer; (c) measuring the total fluid pressure within the cell chamber; and (d) varying the variable gas output of the electrolyzer based on the measured total fluid pressure.

In a more detailed feature of the invention, the electrolyzer may be a water electrolyzer, and the gas may be oxygen.

In a more detailed feature of the invention, the measuring and varying steps may be performed automatically without requiring operator intervention.

In a more detailed feature of the invention, the measuring step may comprise using a total fluid pressure sensor.

In a more detailed feature of the invention, the total fluid pressure sensor may be disposed within the cell capsule.

In a more detailed feature of the invention, the total fluid pressure sensor may be disposed outside of the cell capsule.

In a more detailed feature of the invention, the water electrolyzer, the cell capsule, and the total fluid pressure sensor may be subcutaneously implanted in a subject.

In a more detailed feature of the invention, the varying step may comprise using a controller.

In a more detailed feature of the invention, the water electrolyzer, the cell capsule, the total fluid pressure sensor, and the controller may be subcutaneously implanted in a subject.

The present invention is also directed at a method for controlling oxygen concentration in a cell implant.

According to one aspect of the invention, a method for controlling oxygen concentration in a cell implant comprises the steps of (a) providing an electrochemical cell, the electrochemical cell being configured to operate alternatively in a water electrolyzer mode and in a fuel cell mode; (b) providing a cell capsule, the cell capsule comprising a cell chamber adapted to hold cells, wherein the cell capsule is fluidically coupled to the electrochemical cell; (c) measuring the total fluid pressure within the cell chamber; and (d) operating the electrochemical cell in one of the water electrolyzer mode and the fuel cell mode based on the measured total fluid pressure.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts.

DETAILED DESCRIPTION OF THE INVENTION

The survival and function of implanted cell therapies depend critically on the availability of oxygen to support metabolism. While intravascular engraftment of cells or the integration of cells into well-vascularized capsules results in good exploitation of the recipient extant blood oxygen, there are practical limits to the density or thickness of cells transplanted due to diffusional limits of oxygen transport from the bulk to the mitochondria of all the cells. Because the oxygen tension (partial pressure, $pO_2$) in the blood in the capillary environment of subcutaneous tissue (a useful implantation site) is relatively low (<50 mmHg), there is an especial problem relating to device size, particularly for cells having high oxygen consumption rates and cluster morphologies, such as the islets of Langerhans.

Figure 1:
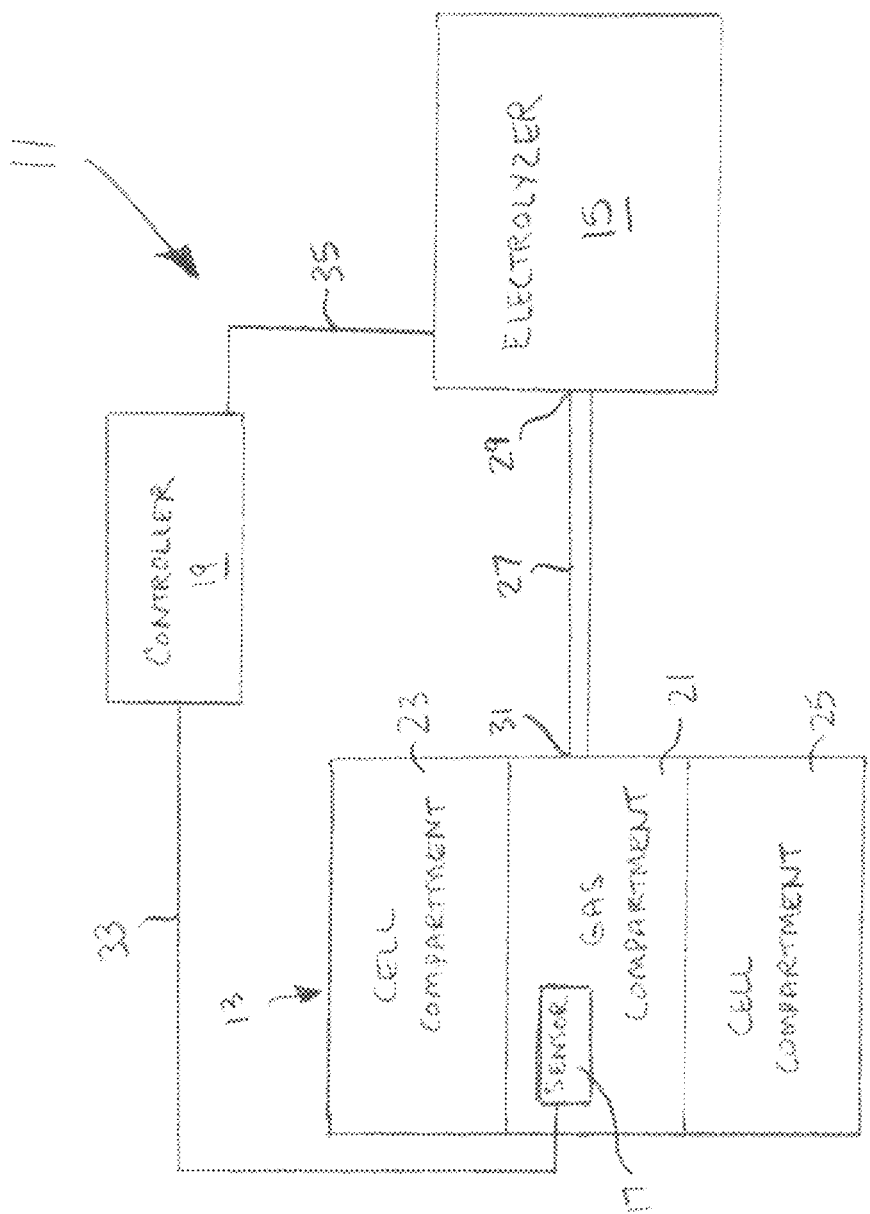
FIG. 1 is a simplified schematic representation of a first embodiment of a system for controlling oxygen delivery to a cell implant, the system being constructed according to the teachings of the present invention.

A solution to the problem of cell survival, function and device size involves the provision of supplemental oxygen to the site of cell transplant, wherein the supplemental oxygen is sufficient to sustain the respiratory needs of all of the cells and allowing for increased cell density in the device. However, a fully implanted device preferably has no percutaneous vent of unused gas; therefore, oxygen delivered to the capsule is ideally terminal at the oxygen diffusion interface to the cells (i.e., dead-ended). Oxygen can be generated in a fully-implanted device by a number of methods, such as water electrolysis, as disclosed, for example, in U.S. Pat. No. 10,231,817 B2. As will be discussed further below, FIG. 1 is a simplified schematic representation of one embodiment of a system for controlled oxygen delivery to a cell implant, wherein the system involves the use of water electrolysis.

Figure 2:
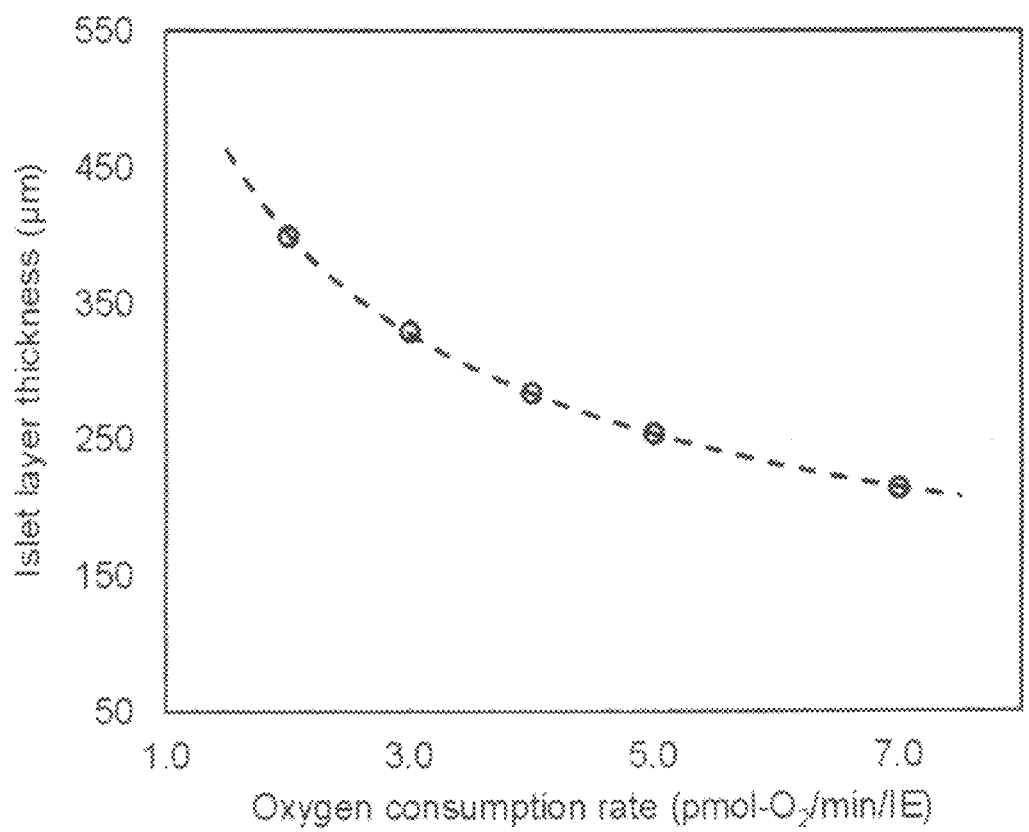
FIG. 2 is a graph depicting maximum calculated tissue thickness in a single cell compartment as a function of islet oxygen consumption rate where limits of insulin response function ($pO_2$>35 mmHg) and hyperoxia ($pO_2$<540 mmHg) are both satisfied and where capsule is assumed to be 75 vol % islet or beta cell tissue.

One-dimensional engineering modelling of cell capsules having a vascularized interface to recipient tissue on one face and supplemental oxygen delivery to the other face suggests that the delivered supplemental oxygen tension and the oxygen consumption rate of the cells should be matched to support the limits of hypoxic damage to or death of interior cells and hyperoxic damage to cells near the oxygen delivery face. Additionally, such modelling suggests that there is a range of cell density (% tissue, number of cell layers depth) that can be supported under any particular set of these input conditions (FIG. 2). Due to extant nitrogen (570 mmHg) and carbon dioxide (50-150 mmHg) diffusion from the blood and the cell layers, there is typically higher-than-ambient pressure in the dead-ended gas compartment of the cell capsule in the steady-state, such that oxygen delivered has sufficient partial pressure to sustain diffusion to the cell layers.

Since the number of islets (reported in islet equivalents, or IE, averaging approximately 1560 cells and a diameter of 150 μm) that comprise a curative dose (assumed here to be 300,000 IE) can be clinically evaluated, and the oxygen consumption rate (OCR) of those cells is known to be in the range of about 2-10 pmol-$O_2$/IE/min, the relationship between cell density, delivered oxygen tension and capsule size is well-bounded. Nevertheless, the OCR of the cells at various depths may vary substantially during the normal rhythms of life, for example, as the capsule ages and densifies, and as environmental changes that may affect, for instance, blood pressure, blood flow, or subcutaneous temperature, ensue. Because the long-term viability of the islet cells depends critically on maintenance of oxygen tension in the range of, minimally, about 35 mmHg (e.g., to avoid cell death or loss of function and support glucose response) and, maximally, about 600 mmHg (e.g., to avoid hyperoxic damage by reactive oxygen species), there should be careful management of oxygen tension in the gas-fed cell capsule. Because the rate of oxygen delivery by an implanted oxygen generator can be varied—e.g., in a water electrolyzer by varying the applied current—there exists a way of programming the generator so as to maintain the oxygen tension within the appropriate limits. Therefore, in accordance with one embodiment of the invention, the total gas capsule pressure may be used for this purpose.

A special case of total gas pressure exists when a gas capsule and cell capsule are separated by a membrane of known oxygen diffusivity and the entire assembly is subjected to normal levels of respiratory (oxygen and carbon dioxide) and inert (i.e., nitrogen) gas partial pressures from the surrounding tissue and supplemental oxygen. Carbon dioxide partial pressures typically do not deviate very significantly in interstitial fluids; consequently, the gas capsule total pressure will be dominated by the approximately 570 mmHg extant nitrogen partial pressure and any additional $pO_2$ required to achieve the necessary diffusive oxygen flux across the membrane to the cell compartment. Water vapor pressure typically will be constant (~47 mmHg) and carbon dioxide typically will be narrowly variable (e.g., about 40-100 mmHg), depending on the level of respiratory activity and the rate of diffusive clearance to host tissue. Calculations based on typical membrane materials and practical cell densities for a bioartificial pancreas application suggest that $pO_2$ maintained in the gas capsule should target about 300-800 mmHg, depending primarily on cell compartment(s) thickness/density and OCR. Thus, for any set of nominal conditions, the total gas compartment steady-state pressure may be about 950-1500 mmHg (3.5-14 psig), and in order to maintain the desired $pO_2$ conditions, the use of a gas pressure sensor in conjunction with the electrolyzer current controller constitutes a simple maintenance strategy. On-off or PID control algorithms may be utilized (see Åkesson, M., & Hagander, P., "Control of Dissolved Oxygen in Stirred Bioreactors," Technical Reports TFRT-7571, Department of Automatic Control, Lund Institute of Technology (LTH) (1998)), and several pressure sensor technologies are amenable. Variations of the PID control algorithm may be used, such as the proportional-integral (PI) algorithm, where no derivative term is employed, or the proportional-derivative (PD) algorithm, where no integral term is employed. Closed-loop control is achieved by applying an algorithm to the difference between the observed total pressure and the total pressure setpoint. This difference (or "error") may be used in the algorithm to scale the change in the current setting or duty cycle (% "on" time) to attain the total pressure setpoint in the system. The benefits of PID control over on-off control include the ability to reach setpoint in a rapid and smooth approach, without "overshoot" or instabilities and with a minimum of hysteresis. An off-control is generally simpler to implement but intrinsically features a sawtooth periodicity due to the lack of intermediate current setting values. In either implementation, closed-loop control allows for relatively close management of oxygen partial pressure delivered to the gas capsule.

In the case of total gas capsule pressure closed-loop control, the sensor may be located in the oxygen delivery tube or inside the gas compartment of a multi-compartment cell container. By far, the most prevalent pressure sensing technology is based on a piezoresistive strain gauge (e.g., the IntraSense® piezoresistive MEMS sensor from Silicon Microstructures, Inc., Milpitas, California). This pressure sensor type, like many other pressure sensor types, involves the placement of a transducing element onto a flexible diaphragm interposed between two sealed compartments, one being a reference and the other being a matrix of interest. When a pressure differential exists between the two compartments, the diaphragm deflects in response, and strain that occurs in the diaphragm material causes, in the case of the piezoresistive element, a change in resistance of one element in a Wheatstone bridge electrical circuit. (See Sandmaier et al., "A square-diaphragm piezoresistive pressure sensor with a rectangular central boss for low-pressure ranges," *IEEE transactions on electron devices*, 40(10): 1754-1759 (1993), which is incorporated herein by reference.) An operational amplifier circuit may be additionally configured to amplify the signal required to balance the bridge, thereby registering a signal corresponding to the pressure difference. The reference pressure can be various sealed or interfaced configurations for different types of sensors: sealed vacuum for absolute pressure transducers; ambient or atmospheric interface for gauge transducers; a second working interface for differential pressure transducers; and a confined gas at pressure for sealed pressure transducers.

Another pressure sensing technique is capacitive sensing, including membrane-integrated and interdigitated types. Similar to a piezoresistive sensor, a capacitive sensor relies on changes in an electrical circuit property upon deformation of a diaphragm in response to pressure differential. (See Sander et al., "A monolithic capacitive pressure sensor with pulse-period output," *IEEE Transactions on Electron Devices*, 27(5):927-930 (1980), which is incorporated herein by reference.) In this case, one or both plates of a capacitor are built into a diaphragm, and separation of these plates causes a decrease in the capacitance value. This change manifests in the variation of a sensible dependent signal, such as the oscillation frequency of a circuit.

Additional information regarding pressure sensors may be found in Yu et al., "Chronically Implanted Pressure Sensors: Challenges and State of the Field," *Sensors*, 14:20620-20644 (2014), which is incorporated herein by reference.

Due to the miniaturizability, stability and simplicity of a total gas pressure sensor, the present inventor believes that the use of a total gas pressure sensor, in concert with a control algorithm driving a current controller that, in turn, powers an implanted water electrolyzer that delivers oxygen to a cell compartment, is a particularly desirable way of managing oxygen delivery to a bioartificial pancreas device using cadaveric islets or stem-cell derived beta cell clusters. The methods and component configurations described herein are similarly amenable and logically extensible to a variety of gas generation technologies, therapeutic (or otherwise useful) gas types, and cell or tissue therapeutic applications, or any combination thereof.

Thus, in a preferred embodiment, the present invention relates to a cell therapy device having elements for precise measurement and control of oxygen delivery to implanted cells and also relates to a method of optimally reacting to changes in oxygen demand in order to maintain long-term viability and function of the implanted cells.

Referring now to FIG. 1, there is shown a simplified schematic representation of a first embodiment of a system for controlling oxygen delivery to a cell implant, the system being constructed according to the teachings of the present invention and being represented generally by reference numeral 11. Details of system 11 that are discussed elsewhere in this application or that are not critical to an understanding of the invention may be omitted from FIG. 1 or the accompanying description herein or may be shown in FIG. 1 and/or described herein in a simplified manner.

System 11 may comprise a cell capsule 13, a water electrolyzer 15, a pressure sensor 17, and a controller 19.

Cell capsule 13 may comprise a conventional cell capsule or container adapted to contain implanted cells and/or tissues or may comprise a similarly suitable cell capsule or container. For example, but without limitation, cell capsule 13 may comprise a cell capsule or container of the type disclosed in any one or more of U.S. Pat. No. 10,231,817 B2, U.S. Patent Application Publication No. US 2018/0135948 A1, and U.S. Patent Application Publication No. US 2018/0318566 A1, all of which are incorporated herein by reference. In a preferred embodiment, cell capsule 13 may be a multi-compartment container of the type comprising a gas compartment 21 and two cell compartments 23 and 25. Gas compartment 21 may be sandwiched between cell compartments 23 and 25 and may be separated therefrom by one or more membranes. Gas compartment 21 may be in gas communication with cell compartments 23 and 25. For example, gas in gas compartment 21 may become soluble (i.e., dissolve) in the one or more membranes separating gas compartment 21 from cell compartments 23 and 25; thereafter, said dissolved gas may enter cell compartment 23 and 25 from gas compartment 21 as a dissolved gas. Examples of cell capsules that may be suitable for use as cell capsule 13 may comprise, but are not limited to, cell containment system 1000 of U.S. Pat. No. 10,231,817 B2 and combined gas diffuser/cell capsule devices 911 and 1011 of U.S. Patent Application Publication No. US 2018/0318566 A1.

Water electrolyzer 15 may comprise a conventional water electrolyzer or may comprise a similarly suitable water electrolyzer. For example, but without limitation, water electrolyzer 15 may comprise a water electrolyzer of the type disclosed in one or more of U.S. Pat. No. 10,231,817 B2, U.S. Pat. No. 6,368,592 B1, U.S. Patent Application Publication No. US 2018/0135948 A1, U.S. Patent Application Publication No. US 2018/0133383 A1, and U.S. Patent Application Publication No. US 2018/0318566 A1, all of which are incorporated herein by reference.

Water electrolyzer 15 may be used to electrochemically generate oxygen (and hydrogen) by splitting water, where the rate of oxygen generation is dictated by the rules of stoichiometry of the electrochemical reaction:

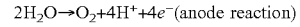

$2H_2O \rightarrow O_2 + 4H^+ + 4e^-$ (anode reaction)

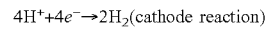

$4H^+ + 4e^- \rightarrow 2H_2$ (cathode reaction)

Therefore, the rate of oxygen generation is controlled by the rate of current flowing to water electrolyzer 15. Controlling current may be performed using current source circuitry in the implanted device using electrical leads connected to the anode (+) and cathode (−) of water electrolyzer 15. The source of water electrolyzed by water electrolyzer 15 may be water from tissue that is vicinal to the implantation site of water electrolyzer 15 or may be some other water source.

A length of tubing 27 or other similarly suitable gas conduit, which may be made of a substantially gas-impermeable material, may be used to fluidically couple an oxygen outlet 29 of water electrolyzer 15 with an oxygen inlet 31 of gas compartment 21 of cell capsule 13. In this manner, oxygen outputted by water electrolyzer 15 may be delivered to cell capsule 13. Hydrogen byproduct, which is also produced by electrolyzer 15, may be delivered from an additional outlet (not shown) on water electrolyzer 15 towards the outside of a subject's body, either by a percutaneous tube or by diffusing into the blood and being expired at the lungs.

Pressure sensor 17 may comprise any sensor capable of sensing total fluid pressure, wherein said fluid may be in the form of a gaseous medium, a liquid medium, or a medium comprising both gas and liquid. For example, but without limitation, pressure sensor 17 may be a conventional piezoresistive-type pressure sensor or a conventional capacitive-type pressure sensor. In the present embodiment, pressure sensor 17 may be disposed within gas compartment 21 of cell capsule 13. Because the fluid located within gas compartment 21 is likely to be substantially entirely a gaseous medium (as opposed to a liquid medium or a medium comprising significant amounts of both liquid and gas), pressure sensor 17 is likely to be tantamount to a gas pressure sensor.

Controller 19, which may comprise a conventional microprocessor or a similarly suitable device, as well as a current source, such as a battery or the like, may be electrically connected with a wire 33 to pressure sensor 17 and may also be connected with a wire 35 to water electrolyzer 15. As will be discussed further below, controller 19 may receive electrical signals from pressure sensor 17 relating to the total fluid pressure within gas compartment 21 and, based on such electrical signals and an algorithm, may control the operation of water electrolyzer 15.

In use, the implanted cells that are contained within compartments 23 and 25 of cell capsule 13 preferably receive oxygen from water electrolyzer 15. One or both of compartments 23 and 25 are preferably positioned sufficiently close to a subject's native vasculature to permit molecular exchange between the implanted cells and the subject's blood. In this manner, nutrients from the blood can be provided to the implanted cells, and secretions from the implanted cells can be provided to the subject for therapeutic effect. At the time of implant, the number of cells required for therapy may be determined as a function of the basal and stimulated needs (e.g., insulin needs) of the subject, and the cells may be loaded into appropriately-sized capsule(s) 13. The capsule loading (cells per unit area of tissue interface) and the oxygen consumption rate (OCR) of the implanted cells may then be used to determine the preliminary oxygen dose (POD, standard cubic centimeters of oxygen per hour, scch) required.

$$POD=1.446\times10^{-6}*n(cells)*OCR/n(islet)$$

where n(cells) is the total number of therapeutic cells required, OCR is the oxygen consumption rate in pmol-$O_2$/IE/min, and n(islet) is the number of cells per islet equivalent (IE, typically 1560 cells/islet). The factor $1.466\times10^{-6}$ is the oxygen mass flow conversion factor between pmol/min and scch.

The preliminary current setpoint ($i_P$) corresponding to the POD is calculated as:

$$i_P=POD*4.5 \text{ mA/scch}$$

wherein the factor 4.5 mA/scch is calculated from Faraday's Law as:

$$i/Q=F*z/V_m$$

wherein Q is the flow rate in scch, F is Faraday's constant (96,485 A-s/mol-e$^-$), z is the transfer number of the electrochemical reaction (mol e–/mol-product; z=4 for electrolytic oxygen production) and $V_m$ is the molar gas volume at standard ambient conditions (24,100 scc/mol-gas; temperature 21° C., pressure 1.0 atmosphere).

As soon as the cells are loaded into capsule 13, system 11 may establish and maintain a current setpoint using controller 19, and the cells may be nourished in culture media (or a similar nutrient medium) during storage, transport and conditioning prior to implant. After implant, the cells may adjust to the nutrient availability inherent to the immediate environment, and, as such, the cells may remodel or suffer apoptosis. Preferably, capsule 13 has surface features that promote growth of plentiful new vascular structures near the cells, and capsule 13 may contain a membrane interposed between the cells and said surface features that prevents the penetration of antibodies into the interior of capsule 13 while still allowing facile transfer of hormones and smaller nutrient molecules. In this way, system 11 may provide a treatment for patients whose bodies are unable to provide sufficiently a key hormone or hormones secreted by the cells.

The signal from pressure sensor 17 may be utilized by controller 19 to inform changes to the current setpoint in order to best prolong the efficacy of the implanted cells, and thereby the duration of beneficial therapeutic effect, without imposing hardship to the patient, such as by the sudden or prolonged release of generated gas into the tissue stemming from overpressurization of or damage to water electrolyzer 15, cell capsule 13, or tubing 27. Controller 19 may have the ability to measure, store and average over multiple time scales (from seconds to months) the voltage or current values corresponding to the pressure value transmitted by pressure sensor 17. Controller 19 additionally may have the ability to control and verify the current applied to water electrolyzer 15. Controller 19 preferably is programmed with an algorithm to respond to changes in observed pressure by changing the current setpoint, per the logic implied by the pressure trend examples and decision tree discussed below.

Figure 3:
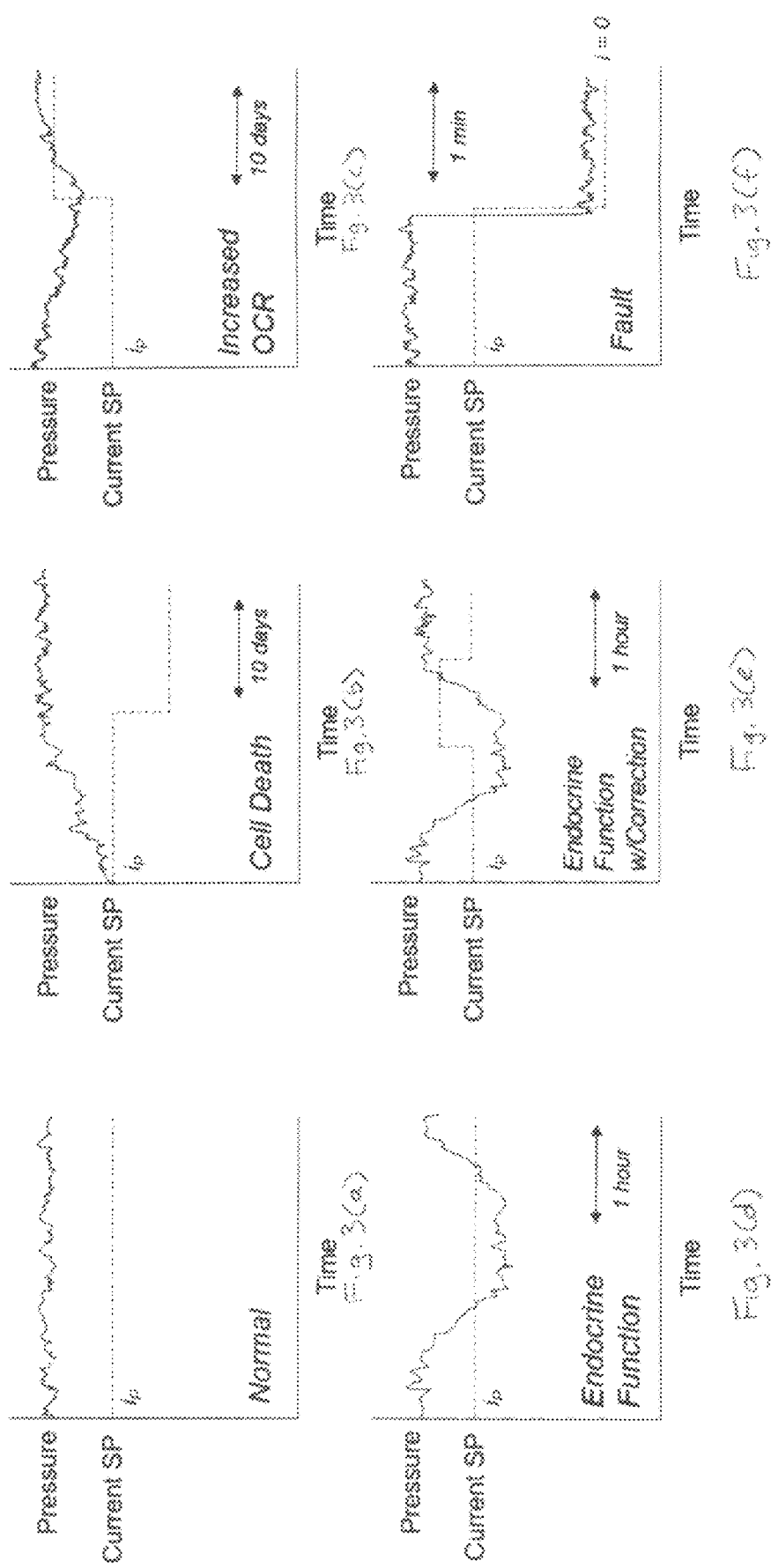
FIGS. 3(a) through 3(f) are graphs depicting proposed changes in current setpoint by the system of FIG. 1 to various scenarios of pressures sensed by the system.

For example, referring now to FIGS. 3(a) through 3(f), there are shown graphs depicting various scenarios that may be encountered during the operation of system 11. For example, in FIG. 3(a), the implanted cells are behaving normally. As a result, the oxygen requirements of the implanted cells substantially match the amount of oxygen that is supplied to the implanted cells by water electrolyzer 15. Consequently, the total gas pressure that is sensed by pressure sensor 17 stays fairly constant, and, accordingly, controller 19 causes the current at which water electrolyzer 15 operates to be kept constant. By contrast, in FIG. 3(b), some of the implanted cells suffer cell distress or cell death. This temporarily causes the amount of oxygen supplied by water electrolyzer 15 to exceed the oxygen requirements of the implanted cells. Consequently, the total gas pressure that is sensed by pressure sensor 17 increases over time. To counter this increase, controller 19 causes the current at which water electrolyzer 15 operates to be reduced to an extent to cause the pressure to stabilize. In FIG. 3(c), the oxygen consumption rate (OCR) of the implanted cells exceeds the amount of oxygen supplied by water electrolyzer 15. This may be due, for example, to cell proliferation or may simply be due to an oxygen consumption that exceeds an initial projection. Because the oxygen consumption rate exceeds the rate at which oxygen is supplied to the implanted cells, the total pressure decreases over time. To counter this effect, controller 19 causes the current at which water electrolyzer 15 operates to be increased to an extent to cause the pressure to return to its initial level. FIG. 3(d) shows the effect of endocrine function. As can be seen, due to an increase in glucose concentration in a subject, there may be a transient increase in the rate of oxygen consumption. Consequently, this causes a corresponding decrease in the pressure sensed by pressure sensor 17 as the oxygen consumption rate outpaces the oxygen supply rate. However, because the increase in oxygen consumption is transient, the total pressure soon resumes its normal level—even without a change in the current at which water electrolyzer 15 operates. FIG. 3(e) shows a scenario that is similar to that of FIG. 3(d), except that, in FIG. 3(e), soon after the decrease in pressure is detected and before self-correction would otherwise occur, controller 19 causes an increase in the current at which water electrolyzer 15 is operated. This increase results in the pressure being restored to its initial level more quickly that it would have otherwise. Then, once the oxygen consumption rate returns to its initial level, controller 19 causes the current at which water electrolyzer 15 operates to be restored to its initial level. In FIG. 3(f), where a fault condition occurs (e.g., fatal malfunction) and the pressure sensed by pressure sensor 17 drops to an unusually low level, controller 19 causes the current to water electrolyzer 15 to be shut off.

Figure 4:
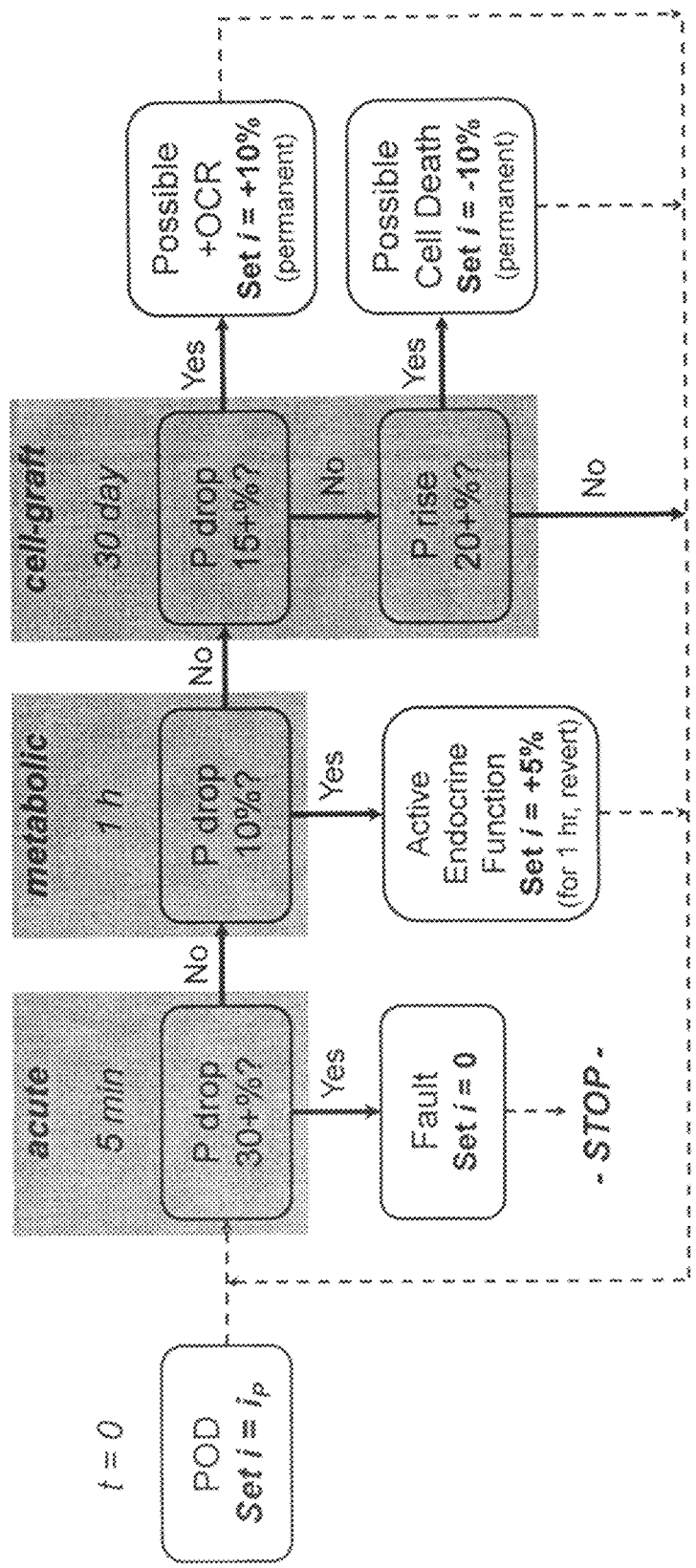
FIG. 4 is a flowchart schematically illustrating the operation of one embodiment of an algorithm employed by the system of FIG. 1.

Referring now to FIG. 4, there is shown a flowchart illustrating the operation of one embodiment of an algorithm employed by system 11 and, in particular, by controller 19.

Controller 19 may, in this example, store running averages ("boxcar" or "first in-first out" buffers) of the implant gas pressure over the following timeframes for decision-making purposes: 5-minute periods at 30-second intervals (acute timeframe); 1 hour periods at 5-minute intervals (metabolic timeframe); 30 day periods at 1-hour intervals (cell-graft timeframe).

The acute timeframe may be utilized to capture sudden, abnormal changes in system pressure, which would be indicative of an acute situation or fault in the system. Controller 19 may appropriately elect to stop delivering gas to the cell capsule at this time (i.e., set the current setpoint to 0) to prevent discomfort or other risks due to subcutaneous emphysema or other problems.

The metabolic timeframe may be utilized to capture changes in pressure which may occur normally as local or global cellular activity slows (i.e., during sleep or cold) or hastens (i.e., during post-prandial endocrine secretion activity, which may be glucose-stimulated). Controller 19 may appropriately elect to increase oxygen production (i.e., set the current setpoint to a temporarily higher value) when pressure drops in this timeframe, so as to mitigate any risk of hypoxia in the cellular graft core. When pressure rises in the timeframe, controller 19 may appropriately elect to decrease oxygen production (i.e., set the current setpoint to a temporarily lower value) when pressure drops in this timeframe, so as to mitigate any risk of hyperoxic damage to cells near the gas compartment of the cell capsule. Alternatively, the oxygen system may be engineered such that its dead volume is sufficient enough that changes to current setpoint are not needed over this timeframe.

The cell-graft timeframe can be utilized to capture changes in pressure which may occur normally as the cells of the implant mature to a higher OCR condition or suffer damage from hypoxia or hyperoxia. Controller 19 may appropriately elect to increase oxygen production (i.e., set the current setpoint to a permanently higher value) when pressure drops in this timeframe, so as to mitigate any risk of hypoxia in the cellular graft core. When pressure rises in the timeframe, controller 19 may appropriately elect to decrease oxygen production (i.e., set the current setpoint to a permanently lower value) when pressure drops in this timeframe, so as to mitigate any risk of hyperoxic damage to cells near the gas compartment of the cell capsule. The cell-graft averaging buffer may optionally be erased upon any permanent change in current setpoint in this timeframe.

The total range of potential current setpoints may be limited to 30%-400% of the $i_P$ determined at the time of implant from POD, and, if desired, no changes to the current setpoint may depart from these limits, except those dictated by an event in the acute timeframe.

In one embodiment of the invention, the entirety of system 11 may be implanted in a subject. In another embodiment of the invention, certain components of system 11 may be implanted in a subject and other components of system 11 may be external to a subject.

Although, in the present embodiment, pressure sensor 17 is disposed within gas compartment 21 of cell capsule 13, it is to be understood that pressure sensor 17 need not be positioned within gas compartment 21 and, instead, may be located at a number of different locations within system 11. This is because the total fluid pressure is fairly constant throughout cell capsule 13, as well as within any fluid conduits coupled to cell capsule 13 and/or to water electrolyzer 15. Various alternative embodiments illustrating this principle are discussed below.

Figure 5:
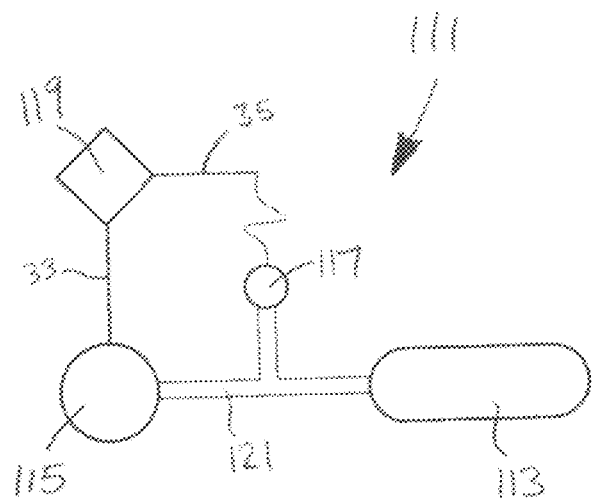
FIG. 5 is a simplified schematic representation of a second embodiment of a system for controlling oxygen delivery to a cell implant, the system being constructed according to the teachings of the present invention.

Referring now to FIG. 5, there is shown a simplified schematic representation of a second embodiment of a system for controlling oxygen delivery to a cell implant, the system being constructed according to the teachings of the present invention and being represented generally by reference numeral 111. Details of system 111 that are discussed elsewhere in this application or that are not critical to an understanding of the invention may be omitted from FIG. 5 and/or the accompanying description herein or may be shown in FIG. 5 and/or described herein in a simplified manner.

System 111 may comprise a cell capsule 113, a water electrolyzer 115, a pressure sensor 117, and a controller 119. Cell capsule 113 may be identical to cell capsule 13, water electrolyzer 115 may be identical to water electrolyzer 15, pressure sensor 117 may be identical to pressure sensor 17, and controller 119 may be identical to controller 19. Wire 33 may electrically couple electrolyzer 115 and controller 119, and wire 35 may electrically couple pressure sensor 117 and controller 119.

System 111 may further comprise a tee-shaped tubing 121 of a substantially gas-impermeable material. A first end of tubing 121 may be fluidically coupled to cell capsule 113, a second end of tubing 121 may be fluidically coupled to water electrolyzer 115, and a third end of tubing 121 may be fluidically coupled to pressure sensor 117.

System 111 may be operated in a manner analogous to that described above for system 11.

Figure 6:
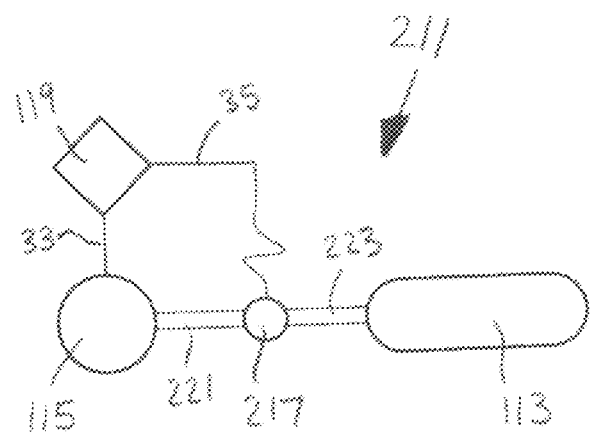
FIG. 6 is a simplified schematic representation of a third embodiment of a system for controlling oxygen delivery to a cell implant, the system being constructed according to the teachings of the present invention.

Referring now to FIG. 6, there is shown a simplified schematic representation of a third embodiment of a system for controlling oxygen delivery to a cell implant, the system being constructed according to the teachings of the present invention and being represented generally by reference numeral 211. Details of system 211 that are discussed elsewhere in this application or that are not critical to an understanding of the invention may be omitted from FIG. 6 and/or the accompanying description herein or may be shown in FIG. 6 and/or described herein in a simplified manner.

System 211 may be similar in many respects to system 111. One difference between the two systems may be that, whereas system 111 may comprise pressure sensor 117, which may have a single fluid port, system 211 may comprise a pressure sensor 217, which may have both a fluid inlet port and a fluid outlet port. Another difference between the two systems may be that, whereas system 111 may comprise tee-shaped tubing 121 fluidically interconnecting cell capsule 113, water electrolyzer 115, and pressure sensor 117, system 211 may, instead, comprise a first length of tubing 221 and a second length of tubing 223. First length of tubing 221 may fluidically interconnect water electrolyzer 115 and a pressure sensor 217, and second length of tubing 223 may fluidically interconnect cell capsule 113 and pressure sensor 217. Each of tubing 221 and tubing 223 may be made of a material similar to that of tubing 121.

System 211 may be operated in a manner analogous to that described above for system 11.

Figure 7:
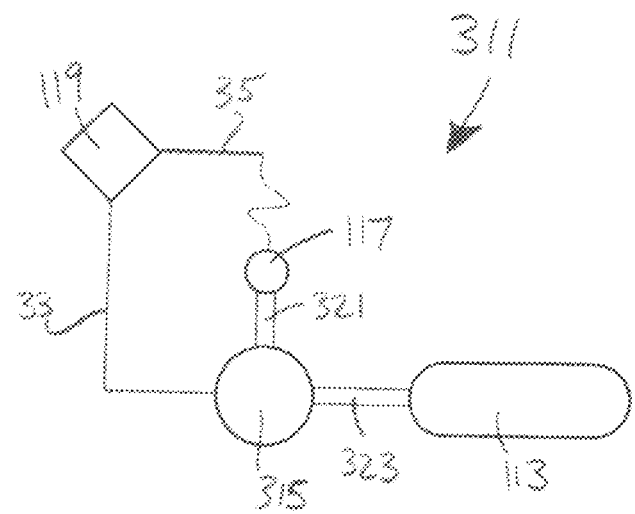
FIG. 7 is a simplified schematic representation of a fourth embodiment of a system for controlling oxygen delivery to a cell implant, the system being constructed according to the teachings of the present invention.

Referring now to FIG. 7, there is shown a simplified schematic representation of a fourth embodiment of a system for controlling oxygen delivery to a cell implant, the system being constructed according to the teachings of the present invention and being represented generally by reference numeral 311. Details of system 311 that are discussed elsewhere in this application or that are not critical to an understanding of the invention may be omitted from FIG. 7 and/or the accompanying description herein or may be shown in FIG. 7 and/or described herein in a simplified manner.

System 311 may be similar in many respects to system 111. One difference between the two systems may be that, whereas system 111 may comprise electrolyzer 115, which may have a single oxygen port, system 311 may comprise an electrolyzer 315, which may have two oxygen ports. Another difference between the two systems may be that, whereas system 111 may comprise tee-shaped tubing 121 fluidically interconnecting cell capsule 113, water electrolyzer 115, and pressure sensor 117, system 311 may, instead, comprise a first length of tubing 321 and a second length of tubing 323. First length of tubing 321 may fluidically interconnect water electrolyzer 315 (at one of its two oxygen ports) and pressure sensor 117, and second length of tubing 323 may fluidically interconnect cell capsule 113 and water electrolyzer 315 (at the other of its two oxygen ports). Each of tubing 321 and tubing 323 may be made of a material similar to that of tubing 121.

System 311 may be operated in a manner analogous to that described above for system 11.

Figure 8:
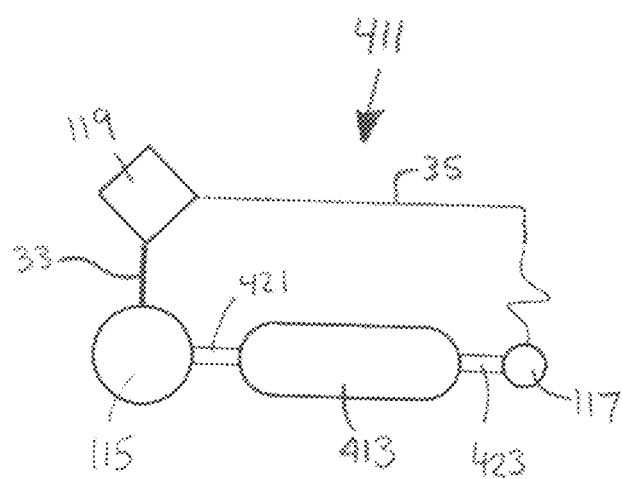
FIG. 8 is a simplified schematic representation of a fifth embodiment of a system for controlling oxygen delivery to a cell implant, the system being constructed according to the teachings of the present invention.

Referring now to FIG. 8, there is a simplified schematic representation of a fifth embodiment of a system for controlling oxygen delivery to a cell implant, the system being constructed according to the teachings of the present invention and being represented generally by reference numeral 411. Details of system 411 that are discussed elsewhere in this application or that are not critical to an understanding of the invention may be omitted from FIG. 8 and/or the accompanying description herein or may be shown in FIG. 8 and/or described herein in a simplified manner.

System 411 may be similar in many respects to system 111. One difference between the two systems may be that, whereas system 111 may comprise cell capsule 113, which may have a single oxygen port, system 411 may comprise a cell capsule 413, which may have two oxygen ports. Another difference between the two systems may be that, whereas system 111 may comprise tee-shaped tubing 121 fluidically interconnecting cell capsule 113, water electrolyzer 115, and pressure sensor 117, system 411 may, instead, comprise a first length of tubing 421 and a second length of tubing 423. First length of tubing 421 may fluidically interconnect water electrolyzer 115 and cell capsule 413 (at one of the two oxygen ports), and second length of tubing 423 may fluidically interconnect cell capsule 413 and water electrolyzer 115 (at the other of the two oxygen ports). Each of tubing 421 and tubing 423 may be made of a material similar to that of tubing 121.

System 411 may be operated in a manner analogous to that described above for system 11.

Figure 9:
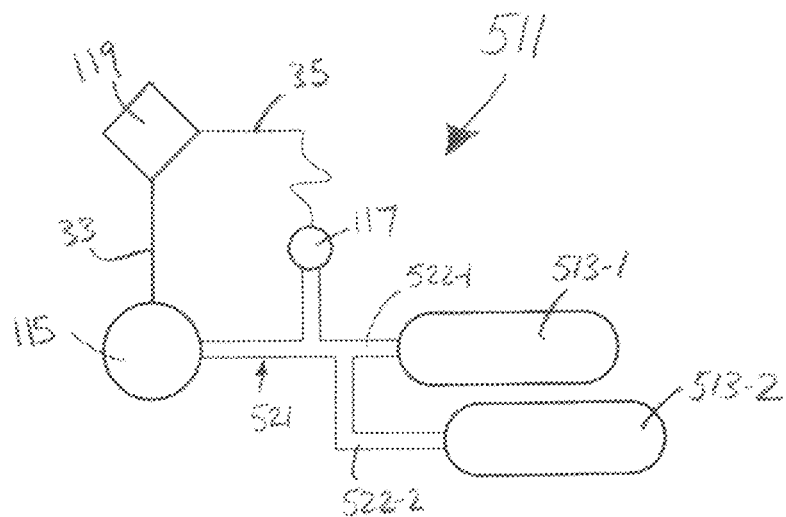
FIG. 9 is a simplified schematic representation of a sixth embodiment of a system for controlling oxygen delivery to a cell implant, the system being constructed according to the teachings of the present invention.

Referring now to FIG. 9, there is a simplified schematic representation of a sixth embodiment of a system for controlling oxygen delivery to a cell implant, the system being constructed according to the teachings of the present invention and being represented generally by reference numeral 511. Details of system 511 that are discussed elsewhere in this application or that are not critical to an understanding of the invention may be omitted from FIG. 9 and/or the accompanying description herein or may be shown in FIG. 9 and/or described herein in a simplified manner.

System 511 may be similar in many respects to system 111. One difference between the two systems may be that, whereas system 111 may comprise a single cell capsule 113, system 511 may comprise two cell capsules 513-1 and 513-2. Each of cell capsules 513-1 and 513-2 may be identical to one another and may be identical to cell capsule 113. Another difference between the two systems may be that, whereas system 111 may comprise tee-shaped tubing 121 fluidically interconnecting cell capsule 113, water electrolyzer 115, and pressure sensor 117, system 511 may, instead, comprise a manifold 521 fluidically interconnecting water electrolyzer 115, pressure sensor 117 and cell capsules 513-1 and 513-2. Manifold 521, which may be made of the same type of material as tubing 121, may be shaped to branch into two legs 522-1 and 522-2 downstream of pressure sensor 117.

System 511 may be operated in a manner analogous to that described above for system 11.

Figure 10:
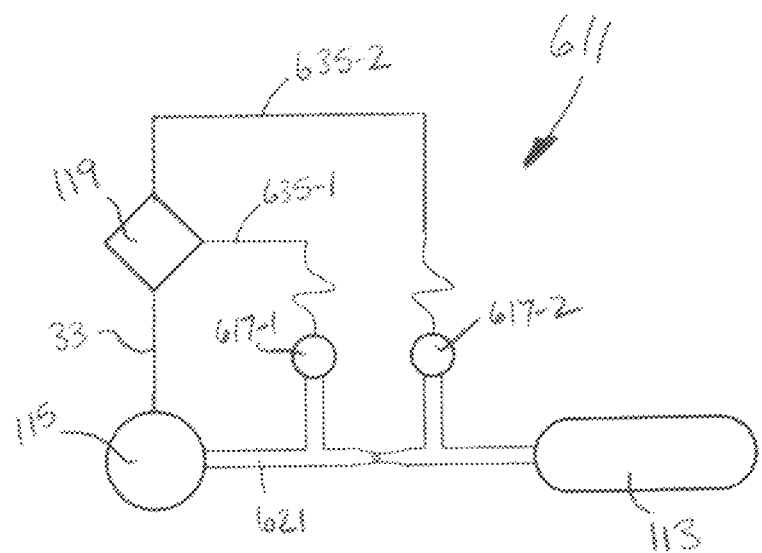
FIG. 10 is a simplified schematic representation of a seventh embodiment of a system for controlling oxygen delivery to a cell implant, the system being constructed according to the teachings of the present invention.

Referring now to FIG. 10, there is a simplified schematic representation of a seventh embodiment of a system for controlling oxygen delivery to a cell implant, the system being constructed according to the teachings of the present invention and being represented generally by reference numeral 611. Details of system 611 that are discussed elsewhere in this application or that are not critical to an understanding of the invention may be omitted from FIG. 10 and/or the accompanying description herein or may be shown in FIG. 10 and/or described herein in a simplified manner.

System 611 may be similar in many respects to system 111. One difference between the two systems may be that, whereas system 111 may comprise a single pressure sensor 117, system 611 may comprise two pressure sensors 617-1 and 617-2. Each of pressure sensors 617-1 and 617-2 may be identical to one another and may be identical to pressure sensor 117. Pressure sensor 617-1 may be electrically coupled to controller 119 by a wire 635-1, and pressure sensor 617-2 may be electrically coupled to controller 119 by a wire 635-2. Another difference between the two systems may be that, whereas system 111 may comprise tee-shaped tubing 121 fluidically interconnecting cell capsule 113, water electrolyzer 115, and pressure sensor 117, system 611 may, instead, comprise a manifold 621 fluidically interconnecting water electrolyzer 115, pressure sensors 617-1 and 617-2, and cell capsule 113. Manifold 621, which may be made of the same type of material as tubing 121, may be shaped to have a constriction with an appropriately configured orifice in the length between the branches for pressure sensors 617-1 and 617-2. In this manner, the difference in pressures read by pressure sensors 617-1 and 617-2 may be used to indicate the fluid flow, and the downstream sensor may be used to indicate total pressure.

System 611 may be operated in a manner similar to that described above for system 11.

As discussed above, the various systems of the present invention are preferably configured so that the oxygen output from the water electrolyzer may be varied in response to the sensed total fluid pressure of the system. For example, this may result in the oxygen output from the water electrolyzer being increased when the sensed total fluid pressure of the system is below a desired level or may result in the oxygen output from the water electrolyzer being decreased when the sensed total fluid pressure of the system is above a desired level. However, there may be situations in which the sensed total fluid pressure of the system is higher than desired, and it may be desirable not only to decrease the oxygen output from the water electrolyzer but to actively remove oxygen from the system (i.e., at a rate faster than the metabolic consumption rate of the implanted cells). In accordance with one embodiment of the invention, this may be accomplished by providing a system that is capable of being alternatively operated in electrolyzer mode or in fuel cell mode. When such a system is operated in electrolyzer mode, the system outputs oxygen, and when such a system is operated in fuel cell mode, the system consumes oxygen. For example, the controller may be configured to operate in a forward (electrolytic) mode in order to develop positive pressure of oxygen by generating gas through the electrolytic reaction, and additionally may be configured to operate in a reverse (fuel cell) mode in order to reduce oxygen pressure by consuming the gas through the discharge of the oxygen and hydrogen in the system by the reverse fuel cell reaction:

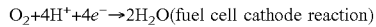

$$O_2 + 4H^+ + 4e^- \rightarrow 2H_2O \text{(fuel cell cathode reaction)}$$

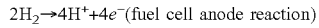

$$2H_2 \rightarrow 4H^+ + 4e^- \text{(fuel cell anode reaction)}$$

The fuel cell mode may be governed by the electronic actuation of a transistor or switch, with an optional series resistor, in parallel with the electrolytic current control circuit, thereby allowing reverse current flow from the electrolyzer, and limited in time of actuation to achieve the desired reduced oxygen pressure. The fuel cell discharge may be used to enhance the rate of gas pressure reduction (i.e., in cases of overpressure during, for instance, diving or an implant system fault), so long as hydrogen gas is available in the open volumes of the electrolyzer cathode compartment, the hydrogen vent tubing and any attached hydrogen gas containing elements. An example of such a system is described below.

Figure 11A:
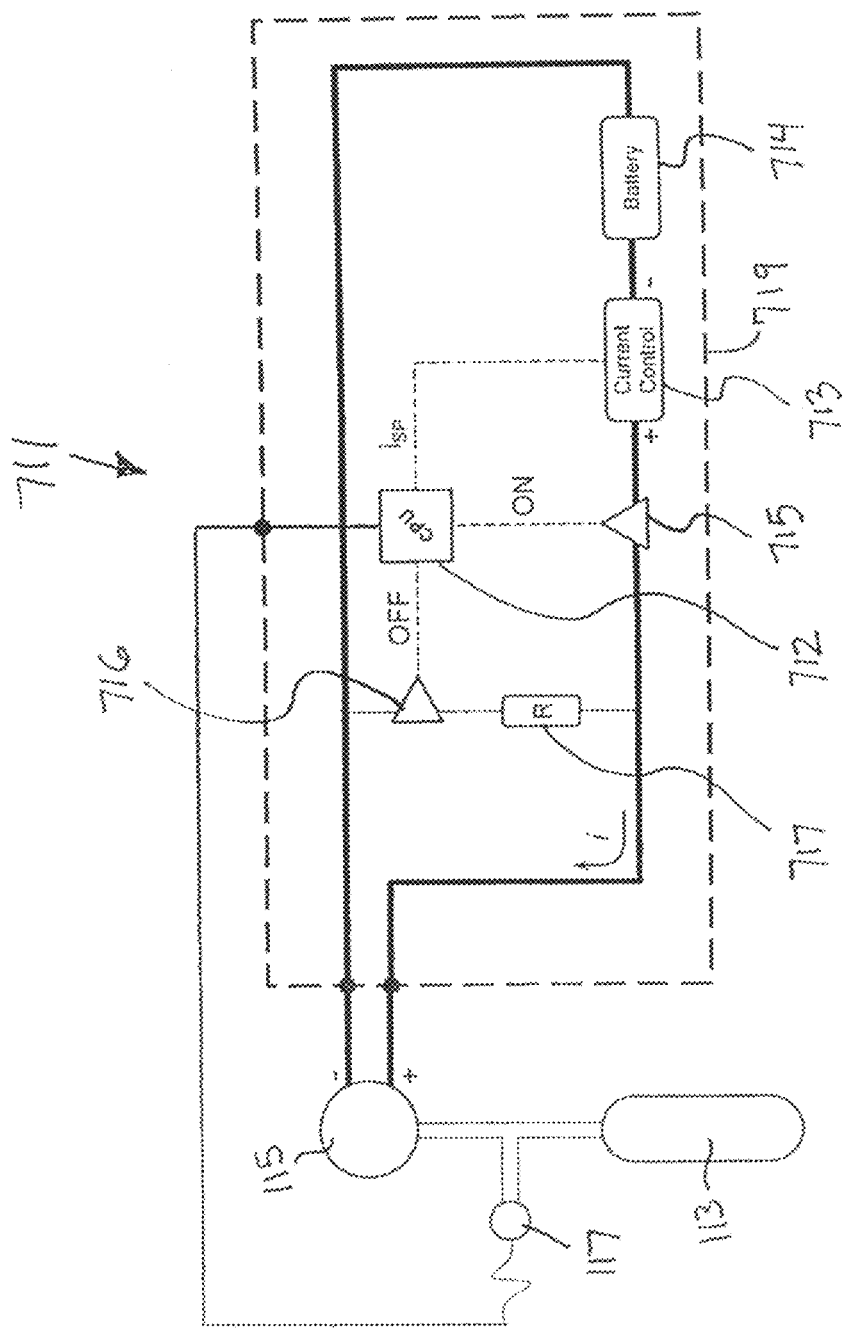
FIGS. 11(a) and 11(b) are simplified schematic representations of one embodiment of a system for controlling oxygen concentration within a cell implant, the system being constructed according to the teachings of the present invention and being shown in electrolyzer and fuel cell modes, respectively.
Figure 11B:
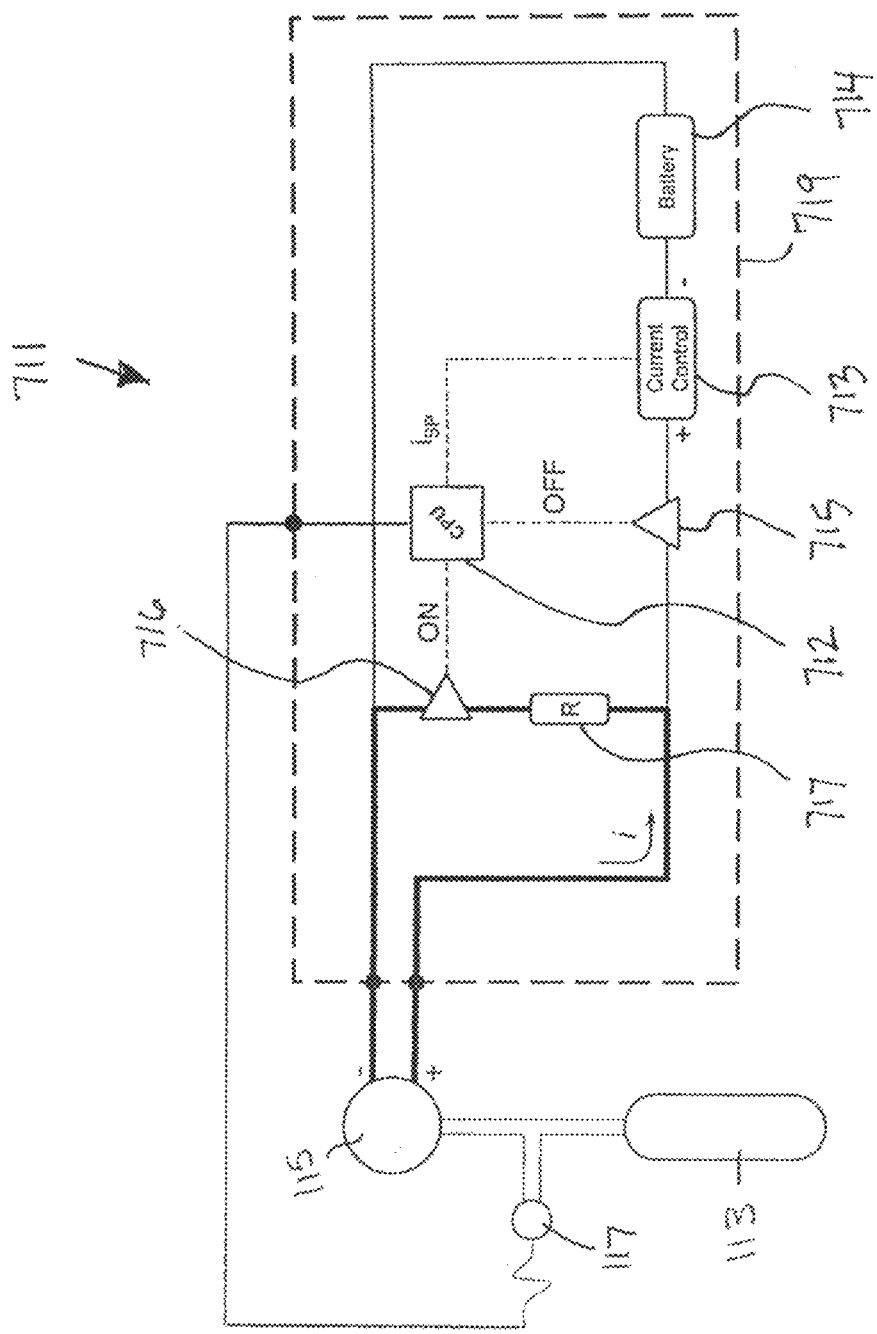

Referring now to FIGS. 11(*a*) and 11(*b*), there are shown simplified schematic representations of one embodiment of a system for controlling oxygen concentration within a cell implant, the system being constructed according to the teachings of the present invention and being represented generally by reference numeral 711. Details of system 711 that are discussed elsewhere in this application or that are not critical to an understanding of the invention may be omitted from one or both of FIGS. 11(*a*) and 11(*b*) and/or the accompanying description herein or may be shown in one or both of FIGS. 11(*a*) and 11(*b*) and/or described herein in a simplified manner.

System 711 may be similar in many respects to system 111. A principal difference between the two systems may be that, whereas system 111 may comprise controller 19, which is configured to operate electrolyzer 115 only in an oxygen-producing mode, system 711 may instead comprise a controller 719, which is configured to operate electrolyzer 115 either in an oxygen-producing mode (i.e., electrolyzer mode) or in an oxygen-consuming mode (i.e., fuel cell mode). More specifically, controller 719 may comprise a microprocessor or similarly suitable device 712 which may be connected to external pressure sensor 117, an internal current controller 713 and electrical switches 715 and 716 enabled (i.e., turned on, such that the two connected wires are short-circuited) by signal wires. The single-pole, single-throw electrical switches used in this application may be any type that are able to create a closed and open circuit condition on the application of a suitable digital or analog signal, such as a mechanical relay (e.g., armature or reed relay) or a semiconductor device such as a solid state relay or field-effect transistor. Controller 719 may further comprise two circuits connected in parallel with the output to electrolyzer 115. The electrolyzer mode circuit may include the current controller 713, the implanted energy source (battery) 714 and the electrolyzer mode enable switch 715, while the fuel cell mode circuit may include the fuel cell mode enable switch 716 and a current-limiting resistor 717. As can be seen in FIG. 11(*a*), the electrolyzer mode of operation may be actuated by turning on the electrolyzer mode switch 715 and turning off the fuel cell mode switch 716 using digital or analog output signals from the microprocessor 712. The electrolyzer current setpoint may be established in the controller 719 by an analog or digital signal from the microprocessor 712 to the current controller 713.

As can be seen in FIG. 11(*b*), the fuel cell mode of operation may be actuated by turning off the electrolyzer mode switch 715 and turning on the fuel cell mode switch 716 using digital or analog output signals from the microprocessor 712. A voltage will exist at the electrolyzer 115 after a period of electrolyzer mode operation due to the presence of oxygen and hydrogen products. This voltage, typically 0.7 to 1.5 volts, provides electrical potential required for current to flow spontaneously, and in a direction opposite to the electrolyzer mode, through the enabled fuel cell mode switch 716 and resistor 717, causing a decrease in oxygen pressure, until hydrogen and/or oxygen activity at the electrolyzer electrochemical interfaces is depleted.

As can readily be appreciated by those skilled in the art of electronic circuitry, an analogous switching configuration can also be arranged by replacing the two single-pole, single-throw electronically-actuated switches with one single-pole double-throw electronically actuated switch, where the common to each throw is connected to the electrolyzer output and the microprocessor signal toggles between shorting the electrolyzer output to the current controller 713 (normally closed, electrolyzer mode) and shorting the electrolyzer output to the parallel circuit loop containing the current-limiting resistor 717.

As can readily be appreciated, the arrangement of water electrolyzer 115, total fluid pressure sensor 117 and cell capsule 113 in system 711 is merely illustrative; thus, the arrangement of these components may be modified along the lines of any of the systems described above.

It is to be understood that features of two or more of the above embodiments may be combined. Moreover, such combinations may share one or more common controllers. Furthermore, the embodiments described above may be used in an analogous fashion to control delivery of other electrolytically-derived gases in other implanted medical applications.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A system for controlling oxygen delivery to a cell implant, the system comprising:
   (a) a water electrolyzer, the water electrolyzer being configured to generate gaseous oxygen with a variable output;
   (b) a first cell capsule, the first cell capsule comprising a first cell chamber adapted to hold cells;
   (c) a first gas conduit, the first gas conduit fluidically coupled to the water electrolyzer and to the first cell capsule, whereby gaseous oxygen generated by the water electrolyzer is delivered to the first cell capsule;
   (d) a first total fluid pressure sensor, the first total fluid pressure sensor being placed so as to sense the total fluid pressure within the first cell chamber of the first cell capsule, wherein the first total fluid pressure sensor comprises a microelectromechanical system (MEMS) sensor and wherein the MEMS sensor relies on changes in an electrical circuit property upon deformation of a diaphragm in response to a pressure differential between the total fluid pressure within the first cell chamber of the first cell capsule and a reference pressure; and
   (e) a controller, the controller comprising a microprocessor electrically coupled both to the first total fluid pressure sensor and to the water electrolyzer, wherein the controller is configured to control current supplied to the water electrolyzer and, thus, to control the variable output of the water electrolyzer based on one or more sensed total pressure readings from the first total fluid pressure sensor, wherein, if the first total fluid pressure sensor senses a total fluid pressure reading that is above a maximum level, the controller causes current supplied to the water electrolyzer to be decreased and, as a result, the variable output of the water electrolyzer to be decreased and wherein, if the first total fluid pressure sensor senses a total fluid pressure reading that is below a minimum level, the controller causes current supplied to the water electrolyzer to be increased and, as a result, the variable output of the water electrolyzer to be increased.

2. The system as claimed in claim 1 wherein the first total fluid pressure sensor is disposed within the first cell capsule.

3. The system as claimed in claim 2 wherein the first cell capsule comprises a gas compartment and a cell compartment, the gas compartment and the cell compartment being in gas communication with one another.

4. The system as claimed in claim 3 wherein the first total fluid pressure sensor is disposed within the gas compartment of the first cell capsule.

5. The system as claimed in claim 1 wherein the first total fluid pressure sensor is disposed outside of the first cell capsule.

6. The system as claimed in claim 5 wherein the first gas conduit is tee-shaped, with a first end of the first gas conduit fluidically coupled to the water electrolyzer, with a second end of the first gas conduit fluidically coupled to the first total fluid pressure sensor, and with a third end of the first gas conduit fluidically coupled to the first cell capsule.

7. The system as claimed in claim 5 further comprising a second gas conduit, the second gas conduit having a first end fluidically coupled to the water electrolyzer and a second end fluidically coupled to the first total fluid pressure sensor.

8. The system as claimed in claim 5 further comprising a second gas conduit, the second gas conduit having a first end fluidically coupled to the first cell capsule and a second end fluidically coupled to the first total fluid pressure sensor.

9. The system as claimed in claim 1 further comprising a second cell capsule, the second cell capsule having a second cell chamber adapted to hold cells, wherein the first gas conduit is further fluidically coupled to the second cell capsule, whereby gaseous oxygen generated by the water electrolyzer is delivered to the second cell capsule.

10. The system as claimed in claim 1 further comprising a second total fluid pressure sensor, wherein the second total fluid pressure sensor is electrically coupled to the controller, wherein the first gas conduit is a manifold comprising a first end fluidically coupled to the water electrolyzer, a second end fluidically coupled to the first cell capsule, a first branch fluidically coupled to the first total fluid pressure sensor, and a second branch fluidically coupled to the second total fluid pressure sensor, and wherein the first gas conduit is constricted between the first and second branches and has an opening sized so that a difference in pressures sensed by the first and second total fluid pressure sensors is indicative of fluid flow therepast.

11. The system as claimed in claim 1 wherein the first total fluid pressure sensor is a miniaturized piezoresistive sensor.

12. A system for controlling oxygen delivery to a cell implant, the system comprising:
   (a) a water electrolyzer, the water electrolyzer being configured to generate gaseous oxygen with a variable output;
   (b) a first cell capsule, the first cell capsule comprising a cell chamber adapted to hold cells;
   (c) a first total fluid pressure sensor, the first total fluid pressure sensor being placed so as to sense the total fluid pressure within the cell chamber of the first cell capsule, wherein the first total fluid pressure sensor comprises a microelectromechanical system (MEMS) sensor and wherein the MEMS sensor relies on changes in an electrical circuit property upon deformation of a diaphragm in response to a pressure differential between the total fluid pressure within the cell chamber of the first cell capsule and a reference pressure;
   (d) a first gas conduit, the first gas conduit fluidically coupled to the water electrolyzer and to the first total fluid pressure sensor;
   (e) a second gas conduit, the second gas conduit fluidically coupled to the first total fluid pressure sensor and to the first cell capsule, whereby gaseous oxygen generated by the water electrolyzer is delivered to the first cell capsule via the first gas conduit, the first total fluid pressure sensor, and the second gas conduit; and
   (f) a controller, the controller comprising a microprocessor electrically coupled both to the first total fluid pressure sensor and to the water electrolyzer, wherein the controller is configured to control current supplied to the water electrolyzer and, thus, to control the variable output of the water electrolyzer based on one or more sensed total pressure readings from the first total fluid pressure sensor, wherein, if the first total fluid pressure sensor senses a total fluid pressure reading that is above a maximum level, the controller causes current supplied to the water electrolyzer to be decreased and, as a result, the variable output of the water electrolyzer to be decreased and wherein, if the first total fluid pressure sensor senses a total fluid pressure reading that is below a minimum level, the controller causes current supplied to the water electrolyzer to be increased and, as a result, the variable output of the water electrolyzer to be increased.

13. A method for controlling delivery of a gas to a cell implant, the method comprising the steps of:
    (a) providing an electrolyzer, the electrolyzer having a variable gas output;
    (b) providing a cell capsule, the cell capsule comprising a cell chamber adapted to hold cells, wherein the cell capsule is fluidically coupled to the variable gas output of the electrolyzer;
    (c) measuring the total fluid pressure within the cell chamber using a total fluid pressure sensor, the total fluid pressure sensor being placed so as to sense the total fluid pressure within the cell chamber of the cell capsule, wherein the total fluid pressure sensor comprises a microelectromechanical system (MEMS) sensor and wherein the MEMS sensor relies on changes in an electrical circuit property upon deformation of a diaphragm in response to a pressure differential between the total fluid pressure within the cell chamber of the cell capsule and a reference pressure; and
    (d) varying the variable gas output of the electrolyzer based on the measured total fluid pressure, wherein the varying step comprises using a controller, the controller comprising a microprocessor electrically coupled to the total fluid pressure sensor and the electrolyzer, wherein the controller is configured to control current supplied to the electrolyzer and, thus, to control the variable gas output of the electrolyzer based on one or more sensed total pressure readings from the total fluid pressure sensor, wherein, if the total fluid pressure sensor senses a total fluid pressure reading that is above a maximum level, the controller causes current supplied to the electrolyzer to be decreased and, as a result, the variable gas output of the electrolyzer to be decreased and wherein, if the total fluid pressure sensor senses a total fluid pressure reading that is below a minimum level, the controller causes current supplied to the electrolyzer to be increased and, as a result, the variable gas output of the electrolyzer to be increased.

14. The method as claimed in claimed in claim 13 wherein the electrolyzer is a water electrolyzer and wherein the gas is oxygen.

15. The method as claimed in claim 14 wherein the measuring and varying steps are performed automatically without requiring operator intervention.

16. The method as claimed in claim 13 wherein the total fluid pressure sensor is disposed within the cell capsule.

17. The method as claimed in claim 13 wherein the total fluid pressure sensor is disposed outside of the cell capsule.

18. The method as claimed in claim 17 wherein the electrolyzer, the cell capsule, and the total fluid pressure sensor are subcutaneously implanted in a subject.

19. The method as claimed in claim 17 wherein the electrolyzer is a water electrolyzer, and wherein the water electrolyzer, the cell capsule, the total fluid pressure sensor, and the controller are subcutaneously implanted in a subject.

20. A method for controlling oxygen concentration in a cell implant, the method comprising the steps of:
    (a) providing an electrochemical cell, the electrochemical cell being configured to be switchable between a water electrolyzer mode, in which oxygen is produced by the electrochemical cell, and a fuel cell mode, in which oxygen is consumed by the electrochemical cell;
    (b) providing a cell capsule, the cell capsule comprising a cell chamber adapted to hold cells, wherein the cell capsule is fluidically coupled to the electrochemical cell;
    (c) measuring the total fluid pressure within the cell chamber; and
    (d) initially operating the electrochemical cell in the water electrolyzer mode when the measured total fluid pressure within the cell chamber is below a desired minimum level and then operating the electrochemical cell in the fuel cell mode when the measured total fluid pressure within the cell chamber is above a desired maximum level.

* * * * *